United States Patent [19]

Brunnquell

[11] Patent Number: 5,520,938
[45] Date of Patent: May 28, 1996

[54] LOW CHOLESTEROL EGGS AND METHOD OF SELECTING SAME

[75] Inventor: John R. Brunnquell, Port Washington, Wis.

[73] Assignee: Wisconsin Alumni Research Foundation, Madison, Wis.

[21] Appl. No.: 326,139

[22] Filed: Oct. 19, 1994

Related U.S. Application Data

[63] Continuation of Ser. No. 161,211, Nov. 30, 1993, abandoned, which is a continuation-in-part of Ser. No. 91,701, Jul. 14, 1993, abandoned.

[51] Int. Cl.$^6$ .............................. A23L 1/32; A01K 43/00
[52] U.S. Cl. ........................... 426/106; 119/68; 209/510; 356/52; 426/298; 426/614
[58] Field of Search .............................. 426/2, 106, 298, 426/614, 807, 830; 53/235, 246–248; 229/2.5; 356/52, 54, 60, 69, 64; 206/521.1, 521.15; 209/510; 119/6.8

[56] References Cited

U.S. PATENT DOCUMENTS

| | | |
|---|---|---|
| 3,153,288 | 10/1964 | Abel et al. . |
| 3,224,559 | 12/1965 | Scollard et al. . |
| 3,661,317 | 5/1972 | Noguchi ................................. 229/2.5 |
| 5,091,195 | 2/1992 | Havens ..................................... 426/2 |

FOREIGN PATENT DOCUMENTS

| | | |
|---|---|---|
| 0006396 | 1/1980 | European Pat. Off. . |
| 57-115159 | 7/1982 | Japan ..................................... 426/614 |
| 61-227743 | 10/1986 | Japan ..................................... 426/614 |

OTHER PUBLICATIONS

STN Abstract AN 76(09):Q0137 FSTA for Godfrey et al. Nutrition Reports International. 1976. 13(3) pp. 263–271.
STN Abstract AN 88:1592 CABA for Rybina et al. Referativny: Zhurnal, 1986. 10(58) p. 216.
Stadelman et al. 1977 Egg Science and Technology. 2nd Ed. AVI Publishing Co. Westport, Conn. p. 102.
Rombauer et al. 1975 Joy of Cooking. Bobbs—Merrill Company, Inc. New York. p. 543.
Lake et al. 1980. Foods and Nutrition, Mills & Boon London. p. 291.
Abstract of Article from Iraqui Journal of Agricultural Sciences, vol. 2, No. 4. p. 7–12, published in 1986 by Derwent Information Ltd., Accession No. 86:2836.
V. Lazar, *egg industry* pp. 18–20 Sep./Oct. (1993) "Bringing sunshine into the hen house is just the beginning . . . the end is contented hens laying more eggs".
M. van Kampen, (Aug. 1982) Heat Stress, Feed Restriction, and the Lipid Composition of Egg Yolk.
Database WPI–Week 8033–Durrent Publications Ltd., London, GB; ANAB–1243 and SUA 705333 (Kompleks Poultry) 28 Dec. 1979 Abstract.
An Apr. 13, 1989 Ozaukee Press article (p. 1), no by–line, "Lower Cholesterol Egg Worth Crowing About".
M. Adams et al., 69 J. Assoc. Off. Anal. Chem. 844–846 (1986) ("Evaluation of Direct Saponification Method for Determination of Cholesterol in Meats").
S. Hussein et al., 72 Poultry Science 595–597 (1993) ("Effect of Age on the Yolk to Albumen Ratio in Chicken Eggs").
50 Poultry Science 1305 (1971) (author unknown) ("Cholesterol Content of Eggs").
I. Hall et al., 33 British Poultry Science 941–946 (1992) ("Variation in Egg Yolk Cholesterol Concentration Between and Within Breeds of the Domestic Fowl").
K. Washburn et al., 56 Poultry Science 1677 (1977) ("Relationship of Yolk and Plasmid Cholesterol Levels to Position of Egg in Clutch").
E. Naber, Cholesterol Content of Eggs, 62 Feedstuffs 50 (1990).
Article in the Mar. 1, 1993 Poultry Times issue, at p. 6, entitled "New Computers May Make Sorting Eggs Easier".

*Primary Examiner*—Anthony J. Weier
*Attorney, Agent, or Firm*—Quarles & Brady

[57] ABSTRACT

Reduced cholesterol, low fat eggs are obtained. At least a twenty-five percent reduction in cholesterol is achieved over normal levels for the grade size. The reduction can be achieved by weight monitoring of the egg, size monitoring of the yolk through candling, and selecting eggs from high producing, young, and high clutch chickens.

18 Claims, No Drawings

LOW CHOLESTEROL EGGS AND METHOD OF SELECTING SAME

This application is a continuation of application Ser. No. 08/161,211, filed Nov. 30, 1993 now abandoned which is a continuation-in-part of Ser. No. 08/091,701 filed Jul. 14, 1993 now abandoned.

FIELD OF THE INVENTION

The present invention relates to techniques for producing and selecting low cholesterol chicken eggs. It appears to be especially well suited for use in connection with "large" size eggs.

BACKGROUND OF THE INVENTION

Serum cholesterol has been implicated in connection with atherosclerosis, a form of heart disease. Efforts have therefore been made to lower serum cholesterol. One approach is to alter the diet by reducing cholesterol intake.

A source of dietary cholesterol is chicken eggs. For example, a "large" chicken egg contains on the average 213 milligrams of total cholesterol. Completely eliminating egg product intake would adversely affect many standard food recipes. While egg substitutes are lower in cholesterol, they are usually poor imitations of real eggs from a texture and taste standpoint. They also often differ in other characteristics that are important to consumers. In this regard, egg substitutes often either contain no egg yolks, or they contain egg yolks that have been treated in ways that are detrimental.

Another concern is the embarrassment factor for those who use egg substitutes. When purchasing or using such specialty dietary products there is a risk that private medical conditions will become public knowledge.

Efforts have therefore been made to try to reduce the cholesterol levels in the eggs themselves. One approach is by controlling the diet of chickens by using low fat, high fiber diets, and by reducing the stress levels for chickens (e.g. using reduced and/or red lights; providing a clean environment; reducing the number of chickens per cage). At best, this has lead to "large" eggs which average (in a randomly selected test sample) above 165 mg per 50 g of egg white and yolk.

U.S. regulatory authorities have promulgated rules that will prohibit advertisement of reduced cholesterol levels in foods unless there is at least a twenty-five percent reduction from "normal" levels. Thus, "large" eggs having (on average) 160 mg or less total cholesterol per 50 g of egg white and yolk are highly desired. "Total cholesterol" can be determined using procedures based on M. Adams et al., 69 J. Assoc. Off. Anal. Chem. 844–846 (1986). See also Official Methods Of Analysis (1990), 15th Edition, Method 976.26 AOAC Arlington, Va. The disclosure of these publications, and of all the other publications referred to herein, are incorporated by reference as if fully set forth herein.

There have been attempts to reduce the cholesterol content of eggs using drugs. In fact, sterols and triparanol have achieved greater than 25% reductions in chicken eggs. However, these drugs are not on the GRAS (generally recognized as safe) listing. Thus, their use would cause adverse labeling and sales restrictions, and there may well be safety problems associated with their use.

Candling is a known technique of shining a light through an egg in order to spot cracks or blood spots by viewing the shadow. It has been reported that candling techniques are now being used with computer imaging systems so as to automate defect spotting. See Poultry Times, p. 6, (Mar. 1, 1993). However, the art has not applied candling techniques to assist in selecting low cholesterol eggs.

The need therefore still exists to achieve a 25% or more reduction in total cholesterol in chicken eggs using techniques that do not require the use of sterols, triparanol, or other drugs that are not on the GRAS list.

SUMMARY OF THE INVENTION

In one aspect, the invention provides a container containing at least six (preferably a dozen) chicken eggs. The eggs in the container average at least 1.5 ounce in weight per egg, and the average total cholesterol content of the eggs is less then 125 milligrams per 37.5 gram of egg white and yolk. The cholesterol level is achieved without having to supply to the chicken or chickens that laid the eggs exogenously supplied steroid, sterol, or triparanol and wherein said eggs do not contain exogenously supplied steroid, sterol, or triparanol.

In another aspect, the invention provides a method for selecting from a supply of chicken eggs six chicken eggs which have an average total cholesterol content of 125 mg or less per 37.5 g of egg white and yolk, wherein the eggs average at minimum at least 1.5 ounces in weight per egg. The method includes selecting only those eggs having a weight not more than 0.083 ounces above the minimum average weight; and also candling the supply of eggs to select out eggs having a yolk shadow with an area above a selected size.

Depending upon whether the eggs are medium, large, extra large, or jumbo, the minimum ounce averages per egg can be respectively 1.75, 2, 2.25, or 2.5, and the cholesterol maximum averages less than 145 mg per 43.75 g of egg white and yolk, 165 mg per 50 g of egg white and yolk, 185 mg per 56.25 g of egg white and yolk, or 205 mg per 62.5 g of egg white and yolk, respectively.

In yet another aspect, the invention provides a method for selecting six chicken eggs which have an average total cholesterol content of 165 mg or less per 50 g of egg white and yolk and a total average weight of at least 2 ounces per egg. The method involves selecting only those eggs having a weight of not more than 2.083 ounces and that have been produced by a layer or layers less than 38 weeks old. Preferably the eggs are selected from flocks that on average have a productivity value of at least 80% (at least 80% of the chickens lay eggs on the day of selection). In an even more preferred form, only those eggs are selected where the layer or layers had their diet supplemented with YEA-SACC yeast prior to the laying the eggs, and the eggs are from a Single Comb White Leghorn.

DESCRIPTION OF THE PREFERRED EMBODIMENTS

Breed

The techniques described herein are believed to be applicable to a wide variety of chickens (*Gallus domesticus*), and in particular to high production, commercially prevalent species thereof such as the White Leghorn (preferably the Single Comb White Leghorn) and the New Hampshire. Crosses between these species are also useable. The invention should also have applicability to low cholesterol mutant forms such as that reported in A. Quershi, et al. 34 Nutritional Reports International 457–464 (1986).

Egg Size

In the United States, eggs are graded by weight based on the number of ounces (shell included) per dozen. A "small" egg is 18 to 20.99 ounces per dozen. A "medium" egg is 21 to 23.99 ounces per dozen. A "large" egg is 24 to 26.99 ounces per dozen. An "extra large" egg is 27 to 29.99 ounces per dozen. A "jumbo" egg is 30 or above ounces per dozen. The experiments described below were performed with large eggs. It should be appreciated that the same techniques can be applied to other sizes of eggs.

The large egg is preferred as persons who are on a diet are reluctant to select "extra large" or "jumbo" eggs. Also, medium and small eggs are too small for many consumers to feel that the product has value.

Eggs are first sorted by weight to divide them into the various sizes of small, medium, large, extra large and jumbo. In accordance with the present invention, there is then a further selection in which only those eggs in the lower third of the weight size range (preferably those in the lower sixth of the range) are selected (e.g. for large, below 2.083 ounces per egg).

Yolk Size

In addition to the above type of selection, one can candle (illuminate) the egg in order to determine the area of the shadow that the egg yolk throws. Conventional candling equipment currently used for spotting cracks or fertilized eggs can be used to project the shadow in the usual fashion. However, in accordance with the invention, the candling can project the shadow on a wall that has a bull's eye target type pattern. When the yolk shadow exceeds a selected area, the egg can be selected out.

For example, this shadow can be compared to a selected norm (e.g. one that only selects on average the smallest ⅓ or ⅙th yolk shadow area for the grade). In this regard, almost all of the cholesterol in an egg is in its yolk. Therefore, while selection by overall weight is helpful, a further desirable step involves the selection by yolk size after the initial weight selection.

In the alternative, the shadow can be projected onto computer imaging equipment, and a computer can then calculate even more accurately the overall yolk shadow area.

Young Layers

Eggs collected shortly after a chicken reaches maturity for egg laying typically have the lowest concentration of cholesterol per gram of yolk. The cholesterol concentration in the yolk typically increases over time until the first molt. Thereafter, it drops somewhat (but generally not all the way back to the beginning levels). It then increases again.

Thus, the total cholesterol concentration in the yolk zig-zags upwardly with chicken age, with the lowest cholesterol level being in the youngest chickens. To assist in achieving the results of the present invention it is preferred to select eggs from chickens that are between initial maturity and 38 weeks old. If extremely low levels need to be achieved, the selection could be skewed to the early part of the range (e.g. 80% or more 18 weeks old).

Productivity

The egg in a chicken is believed to be the excess cholesterol deposit site for the chicken. Typically, the more eggs that the chicken lays, the lower the concentration of cholesterol found in the average yolk. As such, it is preferred to select eggs from only flocks averaging over 80% production per day (80% of the chickens lay an egg that day).

Clutch Size

A clutch is the period of consecutive days in which a hen lays an egg. If a hen lays an egg on eight consecutive days, it would have a clutch size of eight. It has been learned that those eggs which appear later in a clutch typically have the lowest concentration of cholesterol. Thus, it is preferred to select eggs from clutch sizes of five or more, with eggs from days 5 or later being selected.

Low Stress

It has been learned that high levels of stress can increase the level of cholesterol in the egg. Under extremely low stress conditions, the cholesterol concentration in the chicken's egg is typically slightly reduced. Techniques that have proved to be of assistance in connection with lowering the level of cholesterol are housing the chickens in indirect light with high fresh air circulation; keeping the chickens caged and not crowded (not on the floor); keeping the cage areas very clean; and periodically providing soothing and relatively quiet music (e.g. classical music) for the chickens.

Diet

When one provides a low fat, high fiber diet to the chicken, cholesterol levels will decrease. A preferred feed contains about twenty to twenty-five pounds per day, per 100 birds, of the following feed: 50–75% corn, 10–30% soy bean meal, grit, standard vitamin, and calcium mix, 2–10% alfalfa, 20–100 gms/ton of niacin, 2 pounds/ton of YEA-SACC 1026 or 1036 yeast (available from All-Tech).

EXAMPLE

Applicants housed 5,600 Single Comb White Leghorns in a barn, and used the following selection process for the unfertilized eggs. They selected eggs only from chickens of 30 weeks or younger, and only eggs between 2 ounces and 2.083 ounces. A flock having over 80% productivity at the time of selection was used.

The standard environment for the chickens was 65°–75° F., with 14–17 hours of light per day. (At week 18 of a chicken's life the light was 14 hours per day, with the light gradually being increased to 17 hours by the 28th week). This "pseudo-spring" further increases production. The birds were caged with an average of at least 54 square inches per bird.

The feed for the birds was 20 gms/ton niacin; 80 pounds/ton dehydrated alfalfa meal; 2 pounds/ton YEA-SACC yeast; about 398 pounds/ton soy bean meal; 120 pounds/ton calcium; 1390 pounds/ton corn; and 10 pounds/ton grit and conventional nutritional requirements for the chicken ("N.R.C": standard vitamins and minerals). Eggs selected using the above procedures were then assayed for total egg cholesterol. The average (over twelve selected large eggs) was 165 milligrams cholesterol per 51.22 g of egg white and yolk (which equals roughly 161 mg on a 50 g basis).

In another separate test, a sample of eggs averaged 159.7 mg cholesterol per 50 g egg white and yolk.

It should be appreciated that the above experiments were primarily intended to achieve the minimum government labelling requirements. Even further reductions in cholesterol content may be desirable. In this regard, the candling selection step can be added so as to further reduce the average cholesterol content.

For various health and regulatory reasons (e.g. 21 C.F.R. §101.9 (1993)) it is also desirable to reduce total fat and saturated fat levels in foods. Surprisingly, the methods of the present invention also provide eggs with reduced levels of total and saturated fat. For purposes of the claims, total fat is determined by the ether extraction method. See e.g. Official Methods Of Analysis, 15th Edition, 925.32 AOAC, (1990).

Typical levels of total fat for prior art chicken eggs average as follows: small ~3.8 gm/egg; medium ~4.2 gm/egg; large ~4.6 gm/egg; extra large ~5.8 gm/egg; jumbo ~6.2 gm/egg. In one test of the present invention, a sample of large eggs achieved an average total fat content of 3.8 grams fat per egg (compared with the normal ~4.6 gm/egg), with the saturated fat portion reduced by more than 10%.

It should be appreciated that only the preferred embodiments have been described above. The following claims should therefore be looked to in order to judge the full scope of the invention.

I claim:

1. A container containing at least six whole chicken eggs, wherein the eggs in the container average at least 1.5 ounce in weight per egg, wherein the average total cholesterol content of the eggs is less than 125 milligrams per 37.5 g of egg white and yolk, and wherein the cholesterol content was achieved without having to supply to a chicken or chickens that laid the eggs exogenously supplied steroid, sterol, or triparanol and wherein said eggs do not contain exogenously supplied steroid, sterol, or triparanol.

2. The container of claim 1, wherein the eggs in the container average at least 1.75 ounces in weight per egg and wherein the average total cholesterol content of the eggs is less than 145 milligrams per 43.75 g of egg white and yolk.

3. The container of claim 1, wherein the eggs in the container average at least 2 ounces in weight per egg and wherein the average total cholesterol content of the eggs is less than 165 milligrams per 50 g of egg white and yolk.

4. The container of claim 3, wherein the average total cholesterol content of the eggs is less than 162 milligrams per 50 g of egg white and yolk.

5. The container of claim 4, wherein the average total cholesterol content of the eggs is less than 160 milligrams per 50 g of egg white and yolk, and the eggs are Single Comb White Leghorn eggs.

6. The container of claim 1, wherein the eggs in the container average at least 2.25 ounces in weight per egg and wherein the average total cholesterol content of the eggs is less than 185 milligrams per 56.25 g of egg white and yolk.

7. The container of claim 1, wherein the eggs in the container average at least 2.5 ounces in weight per egg, and wherein the average total cholesterol content of the eggs is less than 205 milligrams per 62.5 g of egg white and yolk.

8. A method for selecting from a supply of whole chicken eggs six whole chicken eggs which have an average total cholesterol content of 125 mg or less per 37.5 g of egg white and yolk, wherein the eggs average at minimum 1.5 ounces in weight per egg, the method comprising:

selecting only those eggs having a weight not more than 0.083 ounces above the minimum average weight; and candling the supply of eggs to select out and thus not include eggs having a yolk shadow above a selected size.

9. The method of claim 8, wherein the average total cholesterol content is 145 mg or less per 43.75 g of egg white and yolk, the eggs weigh an average of at least 1.75 ounces per egg; and therefore none of the eggs exceeds 1.833 ounces.

10. The method of claim 8, wherein the average total cholesterol content is 165 mg or less per 50 g of egg white and yolk, the eggs weigh an average of at least 2 ounces per egg; and therefore none of the eggs exceeds 2.083 ounces.

11. The method of claim 8, wherein the average total cholesterol content is 185 mg or less per 56.25 g of egg white and yolk, the eggs weigh an average of at least 2.25 ounces per egg; and therefore none of the eggs exceeds 2.333 ounces.

12. The method of claim 8, wherein the average total cholesterol content is 205 mg or less per 62.6 g of egg white and yolk, the eggs weigh an average of at least 2.5 ounces per egg; and therefore none of the eggs exceeds 2.583 ounces.

13. The container of claim 1, wherein the egg white and yolk in the eggs in the container average less than 3.5 gm total fat per egg.

14. The container of claim 2, wherein the egg white and yolk in the eggs in the container average less than 3.85 gm total fat per egg.

15. The container of claim 3, wherein the egg white and yolk in the eggs in the container average less than 3.85 gm total fat per egg.

16. The container of claim 6, wherein the egg white and yolk in the eggs in the container average less than 5.0 gm total fat per egg.

17. The container of claim 7, wherein the egg white and yolk in the eggs in the container average less than 5.5 gm total fat per egg.

18. The container of claim 3, wherein the chicken or chickens that produced the eggs had been fed yeast prior to laying the eggs.

* * * * *